(12) United States Patent
Hatran

(10) Patent No.: US 10,918,840 B2
(45) Date of Patent: Feb. 16, 2021

(54) DRUG DEVICE ELECTROPORATION SYSTEM

(71) Applicant: Hydra Vascular LLC, Scottsdale, AZ (US)

(72) Inventor: Douglas Phat Hatran, Milpitas, CA (US)

(73) Assignee: Hydra Vascular LLC, Scottsdale, AZ (US)

( * ) Notice: Subject to any disclaimer, the term of this patent is extended or adjusted under 35 U.S.C. 154(b) by 787 days.

(21) Appl. No.: 14/678,966

(22) Filed: Apr. 4, 2015

(65) Prior Publication Data

US 2016/0287843 A1 Oct. 6, 2016
US 2019/0001105 A9 Jan. 3, 2019

Related U.S. Application Data

(60) Provisional application No. 61/989,372, filed on May 6, 2014.

(51) Int. Cl.
*A61M 25/10* (2013.01)
*A61L 29/02* (2006.01)
(Continued)

(52) U.S. Cl.
CPC ......... *A61M 25/104* (2013.01); *A61K 9/0009* (2013.01); *A61K 31/337* (2013.01); *A61L 29/02* (2013.01); *A61L 29/085* (2013.01); *A61L 29/16* (2013.01); *A61M 37/00* (2013.01); *A61N 1/327* (2013.01); *A61L 2300/416* (2013.01);
(Continued)

(58) Field of Classification Search
CPC .......... A61M 25/104; A61M 2025/105; A61M 2025/0057; A61M 37/00; A61M 2037/007; A61M 2025/1075; A61M 2025/109; A61M 2037/0007; A61N 1/327; A61N 1/325
See application file for complete search history.

(56) References Cited

U.S. PATENT DOCUMENTS 5,304,120 A   4/1994 Crandell et al.
5,304,121 A * 4/1994 Sahatjian ............... A61F 2/90
                                            604/509

(Continued)

OTHER PUBLICATIONS

Pascual, A., Bush, H. S., & Copley, J. B. (2005). Renal fibromuscular dysplasia in elderly persons. Am J Kidney Dis, 45(4), e63-e66.
(Continued)

*Primary Examiner* — Manuel A Mendez
*Assistant Examiner* — Justin L Zamory
(74) *Attorney, Agent, or Firm* — Jaffery Watson Mendonsa & Hamilton LLP

(57) ABSTRACT

Active Energy Facilitated Drug Delivery platform for delivering therapeutics to biological tissue through electrical conductivity. This delivery method is comprised of an elastic alloy to encase a balloon or drug deposition, where the alloy acts to emit an electric field in aiding and actively allowing the pharmaceutical agent to have enhanced permeation, binding and internalization to cells and the biological matrix. A therapeutic agent is deposited onto a balloon to embody the drug deposition, reservoir whereby the electrical field facilitates the active transfer of a pharmaceutical agent to the target tissue is described.

26 Claims, 11 Drawing Sheets

(51) Int. Cl.
*A61M 37/00* (2006.01)
*A61K 9/00* (2006.01)
*A61K 31/337* (2006.01)
*A61N 1/32* (2006.01)
*A61L 29/16* (2006.01)
*A61L 29/08* (2006.01)

(52) U.S. Cl.
CPC ... *A61L 2300/602* (2013.01); *A61L 2300/606* (2013.01); *A61L 2400/16* (2013.01); *A61M 2025/105* (2013.01); *A61M 2025/109* (2013.01); *A61M 2025/1075* (2013.01); *A61M 2037/0007* (2013.01); *A61M 2205/0216* (2013.01)

(56) References Cited

U.S. PATENT DOCUMENTS

| | | | |
|---|---|---|---|
| 5,507,724 A | 4/1996 | Hofmann et al. | |
| 5,580,575 A * | 12/1996 | Unger | A61K 9/127 424/450 |
| 5,704,908 A | 1/1998 | Hofmann et al. | |
| 5,944,710 A | 8/1999 | Dev et al. | |
| 6,219,577 B1 | 4/2001 | Brown, III et al. | |
| 6,283,951 B1 * | 9/2001 | Flaherty | A61B 17/11 604/164.11 |
| 9,179,936 B2 | 11/2015 | Feld et al. | |
| 9,216,033 B2 | 12/2015 | Feld et al. | |
| 10,524,825 B2 | 1/2020 | Feld et al. | |
| 2002/0040204 A1 * | 4/2002 | Dev | A61N 1/325 604/20 |
| 2003/0018362 A1 * | 1/2003 | Fellows | A61B 18/1492 607/5 |
| 2003/0100886 A1 * | 5/2003 | Segal | A61M 29/02 604/509 |
| 2005/0036946 A1 * | 2/2005 | Pathak | A61K 49/0442 424/9.4 |
| 2005/0215950 A1 * | 9/2005 | Burgmeier | A61M 25/10 604/103.1 |
| 2007/0129720 A1 * | 6/2007 | Demarais | A61N 1/32 606/41 |
| 2007/0129761 A1 * | 6/2007 | Demarais | A61B 17/3478 607/3 |
| 2008/0300610 A1 * | 12/2008 | Chambers | A61B 17/320725 606/159 |
| 2009/0247933 A1 * | 10/2009 | Maor | A61B 18/1492 604/20 |

OTHER PUBLICATIONS

Eisen, H. J., Tuzcu, E. M., Dorent, R., Kobashigawa, J., Mancini, D., Valantine-von Kaeppler, H. A., . . . & Bernhardt, P. (2003). Everolimus for the prevention of allograft rejection and vasculopathy in cardiac-transplant recipients. New England Journal of Medicine, 349(9), 847-858.

Grünwald, V., Seidel, C., Fenner, M., Ganser, A., Busch, J., & Weikert, S. (2011). Treatment of everolimus-resistant metastatic renal cell carcinoma with VEGF-targeted therapies. British journal of cancer, 105(11), 1635-1639.

Textor, S. C., & Lerman, L. (2010). Renovascular hypertension and ischemic nephropathy. American journal of hypertension, 23(11), 1159-1169.

Sahni, V., Choudhury, D., & Ahmed, Z. (2009). Chemotherapy-associated renal dysfunction. Nature Reviews Nephrology, 5(8), 450-462.

Edwards, M. S., Corriere, M. A., Craven, T. E., Pan, X. M., Rapp, J. H., Pearce, J. D., . . . & Hansen, K. J. (2007). Atheroembolism during percutaneous renal artery revascularization. Journal of Vascular Surgery, 46(1), 55-61.

Daemen, J., & Serruys, P. W. (2007). Drug-Eluting Stent Update 2007.Circulation, 116(3), 316-328.

Kastrati, A., Massberg, S., & Ndrepepa, G. (2011). Is Diabetes the Achilles' Heel of Limus-Eluting Stents?. Circulation, 124(8), 869-872.

Alhadad, A., Mattiasson, I., Ivancev, K., Gottsäter, A., & Lindblad, B. (2005). Revascularisation of renal artery stenosis caused by fibromuscular dysplasia: effects on blood pressure during 7-year follow-up are influenced by duration of hypertension and branch artery stenosis. Journal of human hypertension, 19(10), 761-767.

Mousa, A. Y., Campbell, J. E., Stone, P. A., Broce, M., Bates, M. C., & AbuRahma, A. F. (2011). Short and long-term outcomes of percutaneous transluminal angioplasty/stenting of renal fibromuscular dysplasia over a ten-year period. Journal of Vascular Surgery.

Hiramoto, J., Hansen, K. J., Pan, X. M., Edwards, M. S., Sawhney, R., & Rapp, J. H. (2005). Atheroemboli during renal artery angioplasty: an ex vivo study. Journal of vascular surgery, 41(6), 1026-1030.

"QT Vascular: Our Companies." 2020, 1 page, < https://qtvascular.com/us/our-companies/>.

"QT Vascular Announces the Allowance of Four New Patents." Jul. 14, 2015, Singapore, pp. 1-4, <https://qtvascular.com/wp-content/uploads/2016/06/QT-Vascular-Announces-Notice-of-Allowance-on-Four-Patents.pdf>. Press release, PDF download.

U.S. Appl. No. 13/761,525 "Notice of Allowance," dated Jul. 1, 2015, 10 pages.

* cited by examiner

FIG. 5
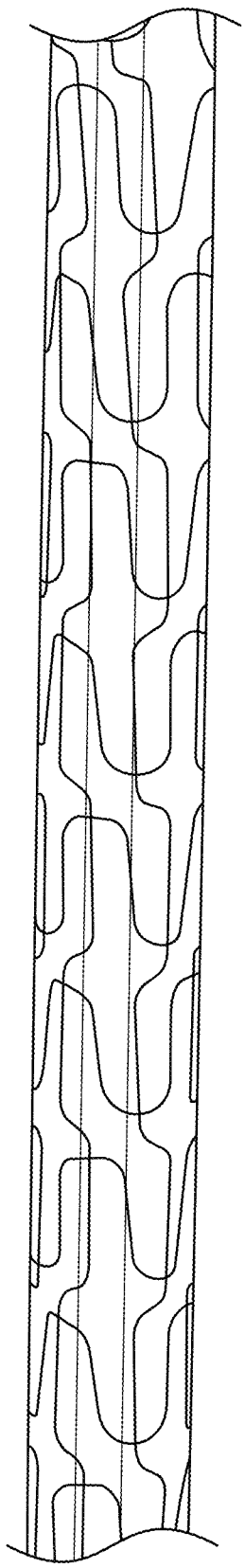
FIG. 6
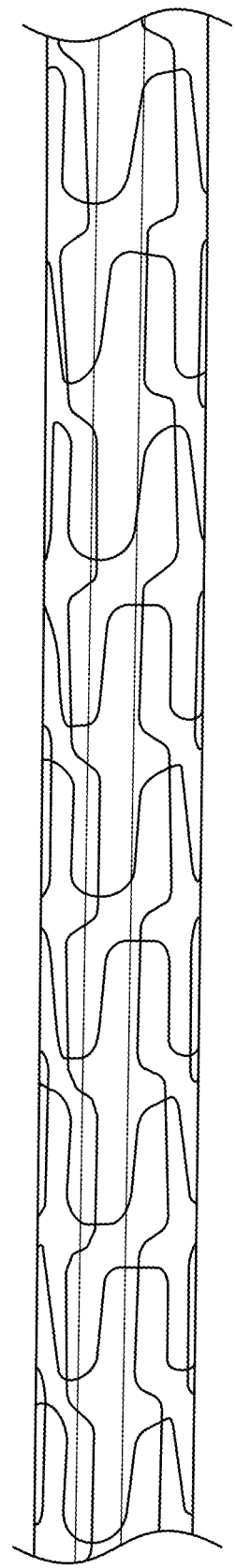

US 10,918,840 B2

DRUG DEVICE ELECTROPORATION SYSTEM

RELATED APPLICATIONS

This application claims the benefit of U.S. Provisional Application No. 61/989,372, filed on May 6, 2014.

TECHNICAL FIELD

Embodiments of the present invention relate generally to the design of a drug device electroporation angioplasty system.

BACKGROUND

The narrowing of the blood vessels is commonly referred to as stenosis or restenosis that can occur after injury to the vessel wall, in example atherosclerotic injury, calcified plaque injury, or revascularization. Surgical procedures such as angioplasty, vascular grafting and transplantation can result in inflammation and/or overcompensation of tissue and result in restenosis. Percutaneous trans-luminal vascular intervention by either angioplasty balloons, atherectomy devices or stents is a frequent cause for restenosis.

Restenosis is mediated by overgrowth of vascular smooth muscle cells and the many smooth muscle cell intermediates as well as fibroblasts and other structural support cells and material in response to injury. This overgrowth is commonly referred to as hyperplasia or excessive neo-intimal growth occluding, or obstructing the flow of blood through the blood vessel. This type of vascular disease gives rise to clinical indications involving organ dysfunctions such as hypertension, cardiac failure, limb loss and chronic pain. Much effort has been made to overcome vascular disease without causing harmful secondary effects from potential and existing treatments.

New therapeutic modalities are needed to avoid unwanted long term complications of standard percutaneous therapies. Drug Coated Balloons (DCB)s were developed in an effort to outperform stenting with the use of anti-stenosis drugs. Cell senescence drugs are used to coat angioplasty balloons and are inflated to deliver drug to localized stenosis lesions in the artery. The senescence of cells at the site of angioplasty presumably prevents neo-intimal growth while allowing the endothelium to return, thereby shielding the smooth muscles from contents in the blood stream that cause inflammation and scar tissue growth. DCBs are still ineffective in the ability to distribute drugs in efficacious concentrations and/or evenly within vessel wall in some anatomical locations. In addition, clinical overexpansion of DCBs are useful to drive the drug into the tissue, but this also causes tissue trauma which can promote a vessel diameter late loss, which is particularly harmful to small vessels, such as the coronaries or leg arteries below the knee.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions. In another aspect, disclosed herein is the use of pharmaceuticals in combination with a modified angioplasty device that will aid the drug delivery into the target location with an electrical pulse commonly known as electroporation.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 1d shows exploded view of the hub connection and cathode connection 132. This illustration is a detailed view of the proximal end of the device or hub connector end of the catheter. The aggregation of the braid fibers will act as an electrical conductor to transfer electric pulses to the intended target.

FIG. 5: First prototype with the ReeKross Balloon acquired from ClearStream Bard.

FIG. 6: Second prototype with a commercially available TriReme Chocolate device.

DETAILED DESCRIPTION OF THE INVENTION

Electroporation, in this application, is purposed to introduce and trap pharmaceutical agents (PA) or biological agents (BA) of interest within or beyond the cell membrane. It is a common Molecular Biology tool to transform cells and or deliver therapeutic agents or foreign components and/or materials into the cellular anatomy and cellular space. In the current invention, using an added electrical component known as electroporation to a DCB to enhance the drug binding efficiency to its target is the principal method for overcoming the problems of both DCBs and stents. Electroporation is a method commonly used in Cell Biology as a method of introducing a foreign material (i.e. DNA, virus, chemical compounds, etc. . . . ) into the intercellular or cytosol space. The mode of electroporation operates by sending an electrical or high voltage, low current electromagnetic pulse across the membrane of the cells or tissue whereby momentarily destabilizing the cellular matrix/membrane and exposing both inter and intracellular channels to any molecules that would otherwise require active transport into the cell or matrix. The current invention has the potential to bypass these shortcomings by efficiently delivering therapeutic agents to the artery without resorting to procedures that result in acute tissue damage or chronic irritation.

Definitions

Stenosis: Narrowing of a tubular structure or blood vessel.

Restenosis: The reoccurrence of stenosis or the re-narrowing of a blood vessel

Hypertension: High blood pressure

Renovascular hypertension: High blood pressure due to narrowing of the arteries that carry blood to the kidneys.

Atrophy: decrease in size or wasting away of a body part or tissue

Hyperplasia: an abnormal or unusual increase in the elements composing a part (as cells composing a tissue)

Electroporation: is a significant increase in the electrical conductivity and permeability of the cell plasma membrane caused by an externally applied electric field.

Chronic Renal Insufficiency: is the slow loss of kidney function over time. The main function of the kidneys is to remove wastes and excess water from the body.

Intercellular: between or among cells

Cytosol: The fluid component of cytoplasm, excluding organelles and the insoluble, usually suspended, cytoplasmic components.

Overstretch: common method of angioplasty whereby the lumen is stretched beyond the resting lumen diameter.

Angioplasty: procedure used to open narrow or blocked coronary (heart) arteries

The concept of using electroporation in the vasculature for delivering drugs and/or materials is realized in this invention by combining an elastic stent-like cage over a drug coated angioplasty balloon in which the cage, a conducting emitter, is expanded transiently to make contact with the target tissue or vascular lumen. The cage 102 acts as an electric conductor over the balloon 110 which when powered from outside the body emits a voltage field, and is comprised of an elastic metal as shown in FIG. 1*a*, and connected to the catheter body 112 (FIG. 1*b*) that is comprised of an electric conducting braid 120 along the catheter body (FIG. 1*c*) and exited at the base of the hub assembly 130 (FIG. 1*d*). The expansion of the drug coated balloon combined with the application of power to the cage enhances the dissolution of the drug coating from the balloon and the transfer of drug into the tissue. The enhanced dissolution of the drug from the balloon during the power cycle obviates the need to over-expand the DCB, and thus delivers the drug while minimizing tissue trauma.

The method of closed circuit to deliver the electric pulse will be such that the body is conducted with the opposite polarity to that of the emitter. The body will be grounded with the anode (−) and the cathode as described in this document will be delivering the pulse. An external power source will deliver and control the amount of energy that is a function of duration, voltage and current. Proof of this concept was performed in living explanted swine arteries in which a closed loop fluid/media was circulated through the artery as shown in FIG. 2. The data is generated via HPLC and shown in FIG. 3. The HPLC Chromatogram shows the detection of the pharmaceutical agent (Paclitaxel) as shown in FIG. 4.

To embody the concept, angioplasty devices "ReeKross", BARD and Chocolate PTA, TriReme Medical were acquired from a commercial source for platform prototyping & development purposes. In one embodiment, the ReeKross balloon catheter was made into a prototype for the cage by helically wrapping fine stainless steel wire around the balloon, and continuing the wire along the catheter body to the proximal end (FIG. 5). In another embodiment, the Chocolate balloon from Trireme Medical, which has a stent like cage over the balloon, was used with the addition of a wire connection from the cage to the proximal end of the catheter (FIG. 6). In both of the above embodiments, the modified catheters were syringe-coated on the balloon with a drug and excipient formulation and allowed to dry thoroughly. Other embodiments of a conductive balloon are also envisioned, such as metal paddles glued to the balloons (see FIGS. 1*e*, 1*f* & 1*g*), or an inherently conductive balloon, such as one made by a plastic containing a conductive filler such as carbon black. Another such embodiment would use a conductive coating applied to the balloon as a base layer on the balloon under the drug containing coating.

Potential suitable drugs to coat the balloon for various clinical indications include anti-neoplastic agents such as paclitaxel and sirolimus, chemo-therapeutic agents such as

*vinca* alkaloids, neurotoxic agents such as botulin toxin, nyloxin or cobroxin, or steroids such as dexamethasone.

Potential suitable excipients are oligomers such as poly (ethyleneglycol) (PEG), polymers such as polyvinylpyrrolidone or hydroxyproplyl cellulose, hydrophilic polyacrylates or methacrylates such as poly-HEMA, citrate esters, urea, iodinated non-ionic contrast agents such as Ultravist 360, shellac, biocompatible surfactants such as PEO-PPO block co-polymers (BASF Poloxamer series) or sorbitan esters, lipids, phospholipids, or other bio-compatible excipients known in the art.

Figure 7:
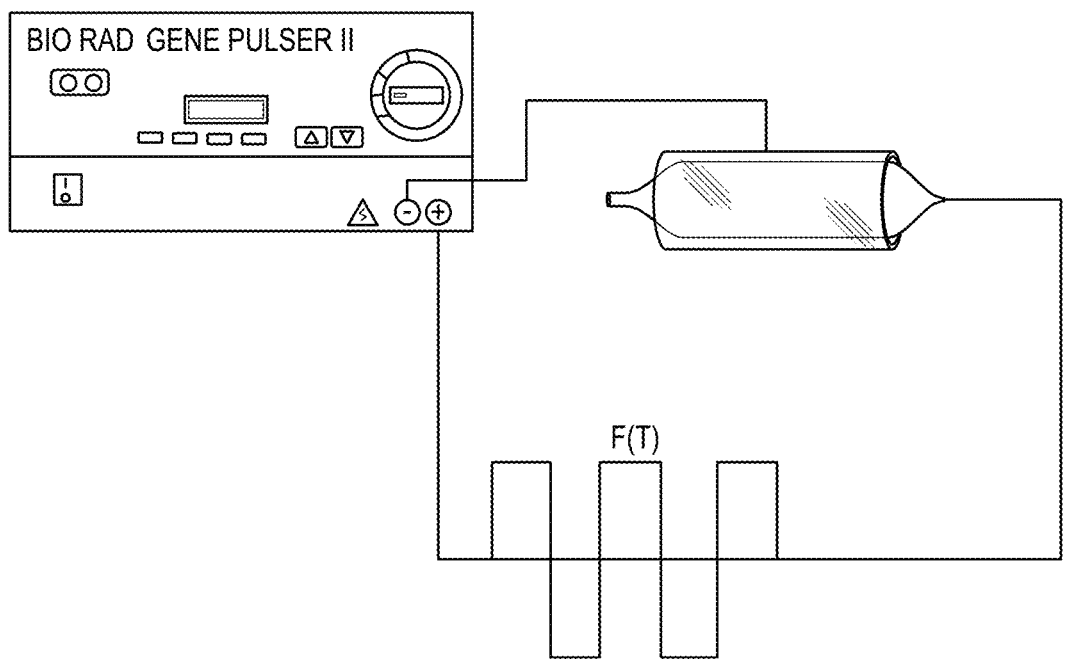
FIG. 7: Gene Pulser II, the energy source acquired and used for delivering energy to transfer PTX onto and into the target tissue.

The energy source to power the device is a pulse generator capable of producing square waves. One commercial example of such a device is the BioRad Gene Pulser II (FIG. 7). The square wave generator produces suitable voltages between the range of 0.001 kV and 5 kV across the membrane. For all prototyping, this device was used to power all of coated catheters by connecting to the wire connection at the proximal catheter end. To demonstrate efficacy ex vivo, living artery tissue was acquired from a CRO, excised by a necropsy technician from the animal (swine) shortly after death. The tissue is then stored in isotonic saline and placed on ice (or 4° C.) for immediate use in an ex-vivo circulatory system.

Ex Vivo Testing

Materials

To perform the ex vivo experiment, the materials required are as follow:

Tygon clear plastic tubing and connectors
Flexible rubber hose tubing or silicon peristaltic pump tubing
Saline solution pellets (100 ml/pellet)
Distilled $H_2O$
Forceps
Surgical Scissors
Suture 2.0 Silk
Peristaltic pump
0.014" compatible guide wire
Latex gloves
Paclitaxel
PolyEthylene Glycol 8000 (PEG 8K
Amber glass vials
Acetone (HPLC Grade)
1 cc & 50 cc Hypodermic needle syringe
1 cc graduated glass pipet
BioRad GenePulser II electroporator
TriReme Chocolate 6.0×40 mm angioplasty balloon
Phenomonex C18 reverse phase column
$H_2O$ (HPLC grade)
Acetonitrile (HPLC grade)
HP 1090 HPLC System with Chemstation
HPLC Column Phenomenex Kinetex 5u C18 50×4.6 mm Part No. 00B4633-E0 S/N: 740719-3
HPLC Guard Column Phenomenex Part No. AJ0-9296

Procedure for Energy Facilitated Drug Delivery

This procedure comprised the steps adhering to the protocol used to generate the proof of concept as it pertains to the data presented in this document. The protocol is subject to modifications for the needs of product development, testing and so forth. In this section the formulation will be discussed followed by the coating process, setup, application and analysis.

Formulation and Coating Process

Stock solution (Solution I): PEG 8k was made at a concentration of 10 mg/ml in Acetone 250 mg Paclitaxel (PTX) was solubilized into 4.125 ml EtOH/Acetone for a final concentration of 60 mg/ml EtOH/acetone (Solution II).

A formulation is made using volumes of Solution 1 and Solution 11 to provide a Drug:PEG-8000 of 5:1.

0.09 ml of the above solution was syringe deposited on a cleaned 6.0×40 Trireme balloon to provide a drug surface coverage of 3.0 ug/mm$^2$.

Ex Vivo Testing Protocol

Fresh PBS is made with pre-measured pellets (1 pellet/100 ml $H_2O$).

Porcine arterial tissue was acquired and cut to length

Arteries are placed in fresh PBS while cleaning of adventitia is performed.

Figure 8:
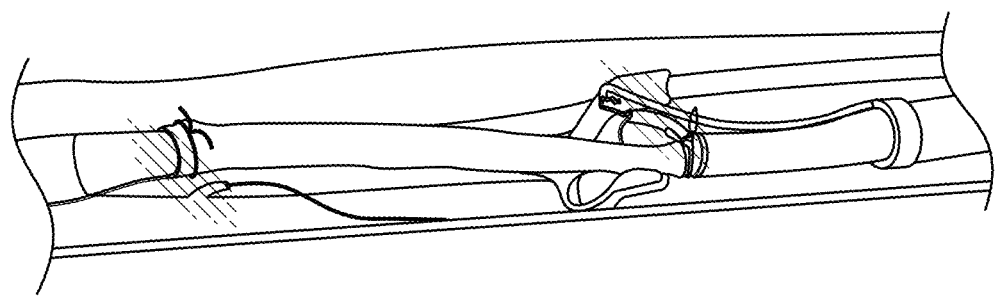
FIG. 8: This is a photograph of the tissue connected to the closed circuit with media flowing through it.

Arteries are attached to the circulation apparatus with cannulas to allow flow through the vessel. (see FIG. 8)

Once connected to the closed flow loop apparatus, the peristaltic pump is commenced to allow circulation to flow for up to 5 minutes.

Continuing with the flow loop (as described in the section for setup 5), a guide wire was used to direct the device path through the flow circuit apparatus and tissue lumen.

The device is connected to the electrical connections of the GenePulserII whereby the cathode was connected to the device and anode was connected to the artery.

The Gene Pulser II was set to 0.5 kV/1 μF

The coated balloon is inserted over the wire and advanced to the target tissue.

Figure 9:
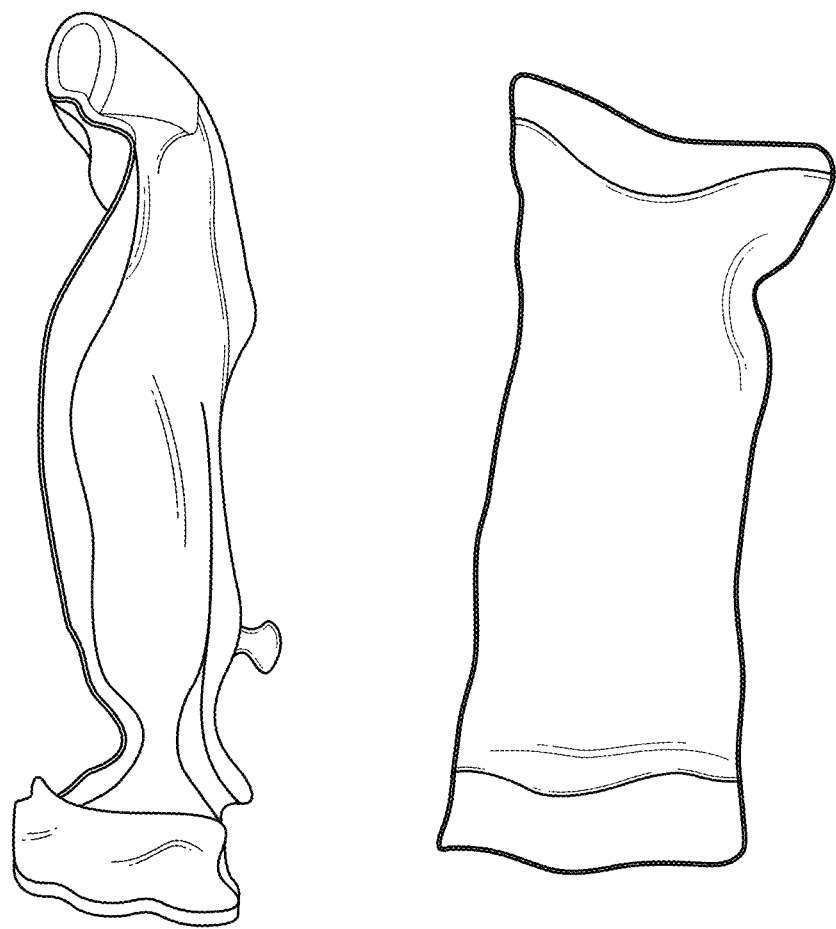
FIG. 9. Shown in this figure are line drawings illustrating how the tissue is opened to expose the lumen to the solvent extraction.

The balloon is expanded to an estimation of a 1:1 balloon to artery ratio whereby the voltage was administered to the target tissue in 3 successions during an approximated 1 minute expansion time. The device is removed and the tissue was resumed with flow for 5 minutes at a rate of approximately 70 mls/minute. The tissue is removed from the apparatus and cut open to expose the lumen and placed into a 5 dram amber vial and labelled accordingly. (see FIG. 9) 3.0 ml of EtOH was added to the vial to extract the PTX from the lumen overnight. The tissue is then removed and placed in mortar pestle and crushed while adding liquid nitrogen until powdered. 3.0-4.0 ml of EtOH was added to extract the PTX from inside the tissue. The ethanol and crushed cell extract were separated via centrifugation whereby the ethanol was removed for analysis.

HPLC Analysis of Paclitaxel in Tissue

The samples are collected and stored at −20° C. HPLC analysis is performed on a C18 column with UV detector. Standards for PTX are generated with each new run by preparing a stock solution of PTX near 1 mg/ml in EtOH and serial diluted to produce a standard curve. Samples are run with the following protocol:

Flow Rate 2 ml/min
Initial Conditions 60% $H_2O$: 40% Acetonitrile
5 minute linear gradient to 60% Acetonitrile
UV detection at 225 nm
5 ul injection volume for Samples and Standards.
HPLC Integration performed on Chemstation
Calculations are performed with the line intercept formula y=mx+b generated from the standard curve.

Example 1

Figure 1A:
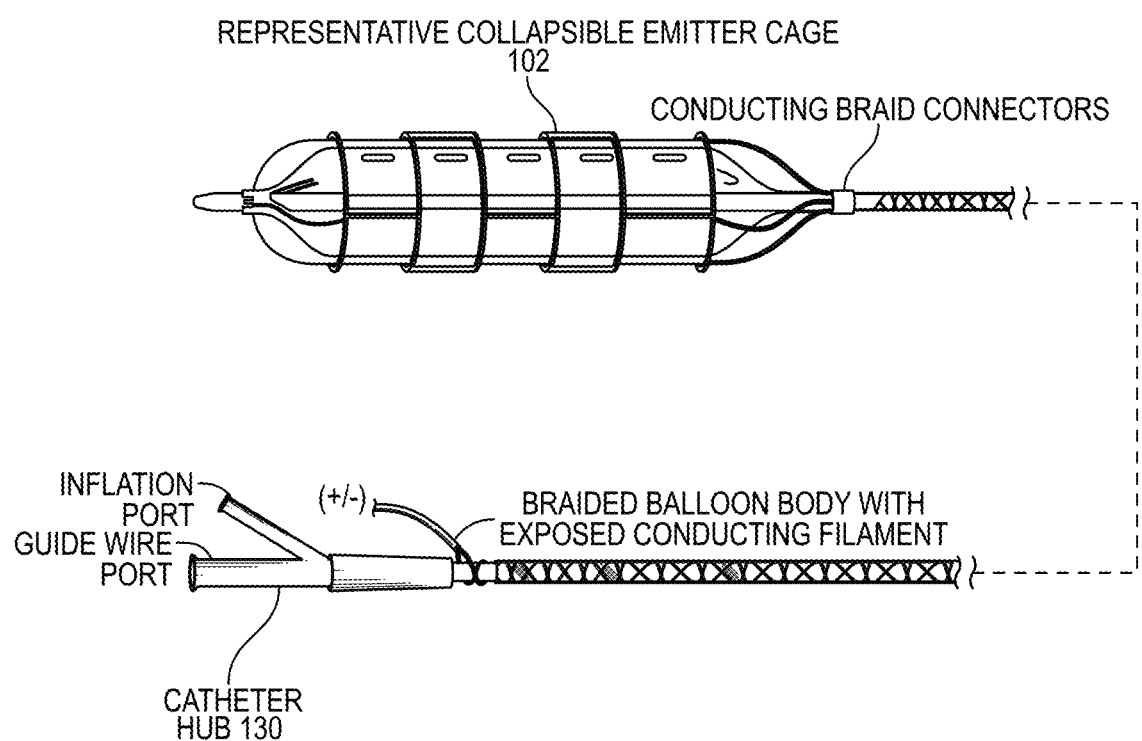
FIG. 1a: Illustration of the overall structure of a balloon and cage. The objects labeled+/−(cathode/anode) are made from any conducting fiber or material thereof (i.e. Copper, Tungsten, Aluminum, carbon based etc. . . . ) for delivering electrical currents by pulsation across the membrane.
Figure 1B:
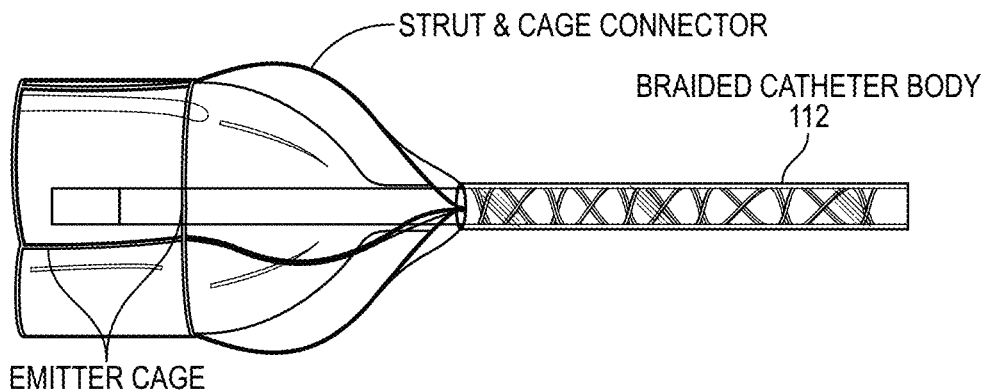
FIG. 1b: The detailed view of the proximal region of the balloon. The conductive braided fiber from the shaft continues to the cage assembly over the balloon. This assembly will be secured to the balloon surface material such that when inflated the balloon and cage will contact the tissue. The polarity can be placed in alternating orientations and is only a representation of the closed circuit formation.
Figure 1C:
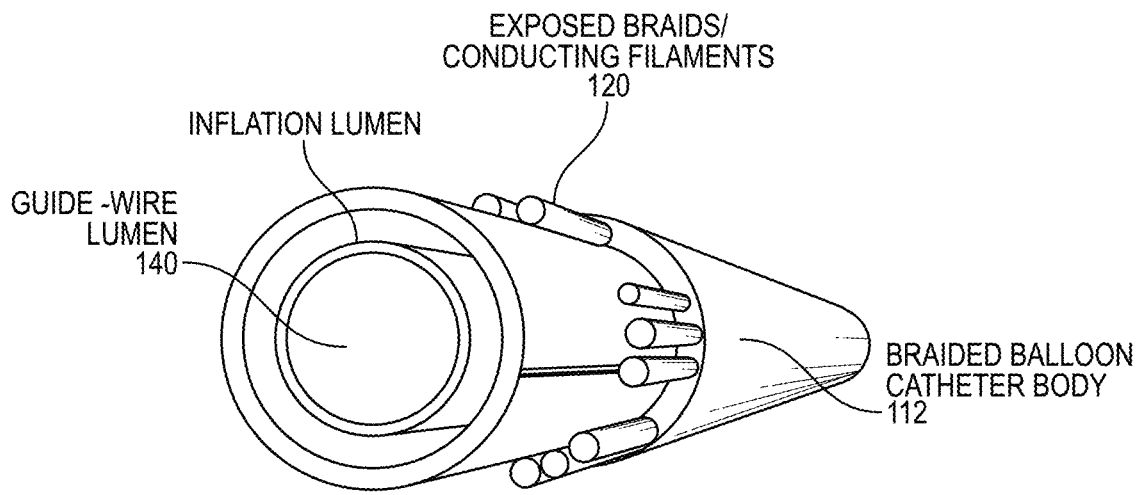
FIG. 1c: Shown is the cross section of the balloon catheter shaft 160 where the electrical conducting material is included in the extrusion process of the material. The "Guide-wire Lumen 140" is the hollow space that allows the vascular intervention wire to pass.
Figure 1D:
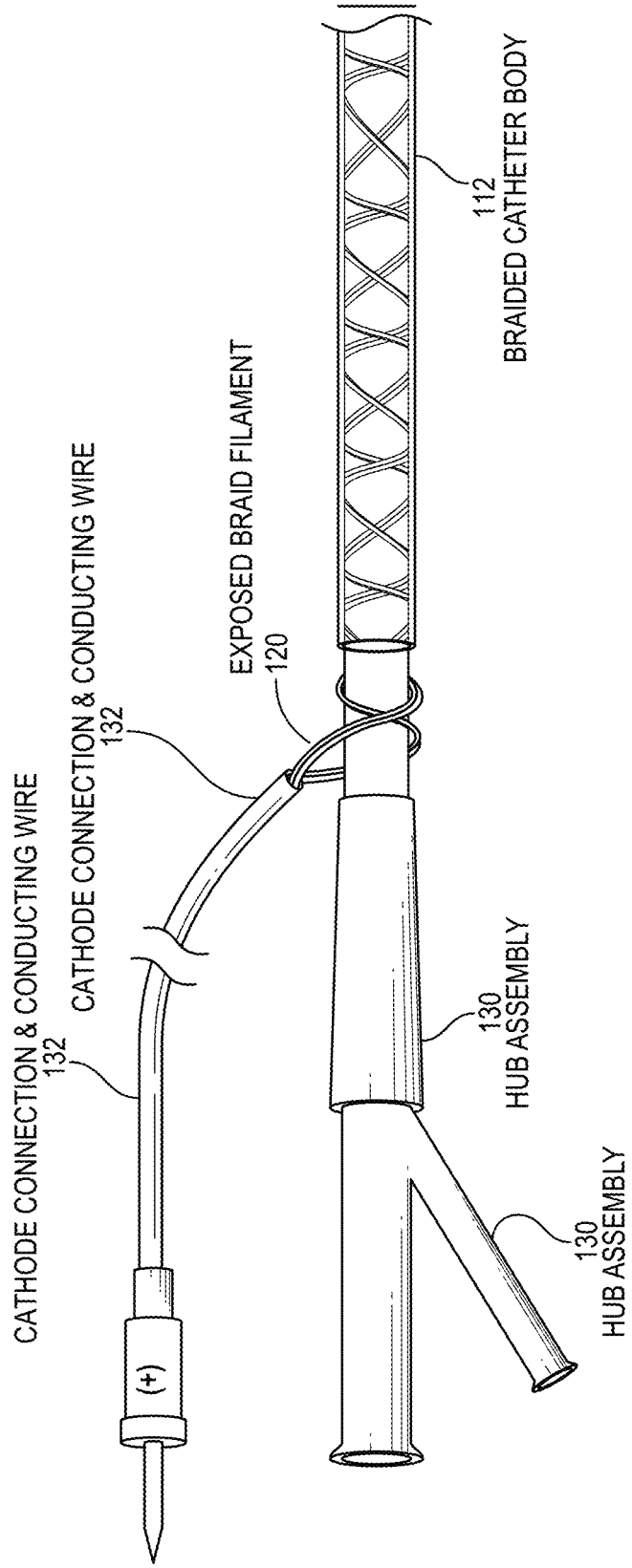
FIG. 1d.
Figure 1E:
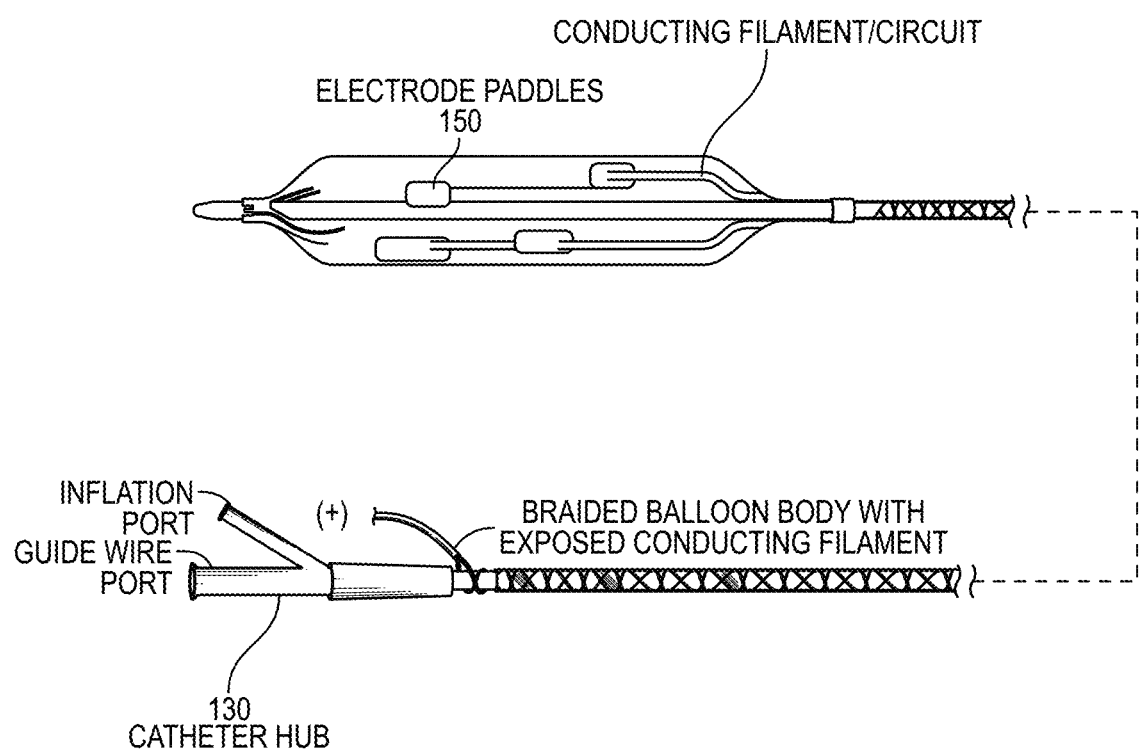
FIG. 1e: Representative drawing of the device with electrical conducting paddles 150 as mentioned in the device description section. This exploded view of the distal tip of the balloon shows the cathode (+) connection. The braided fiber marked with the "+" symbol represents an actual assembly of the distal end whereby the cathode wire will be connected. This assembly will be secured to the balloon surface material whereby the contact points will be direct to the lumen.
Figure 1F:
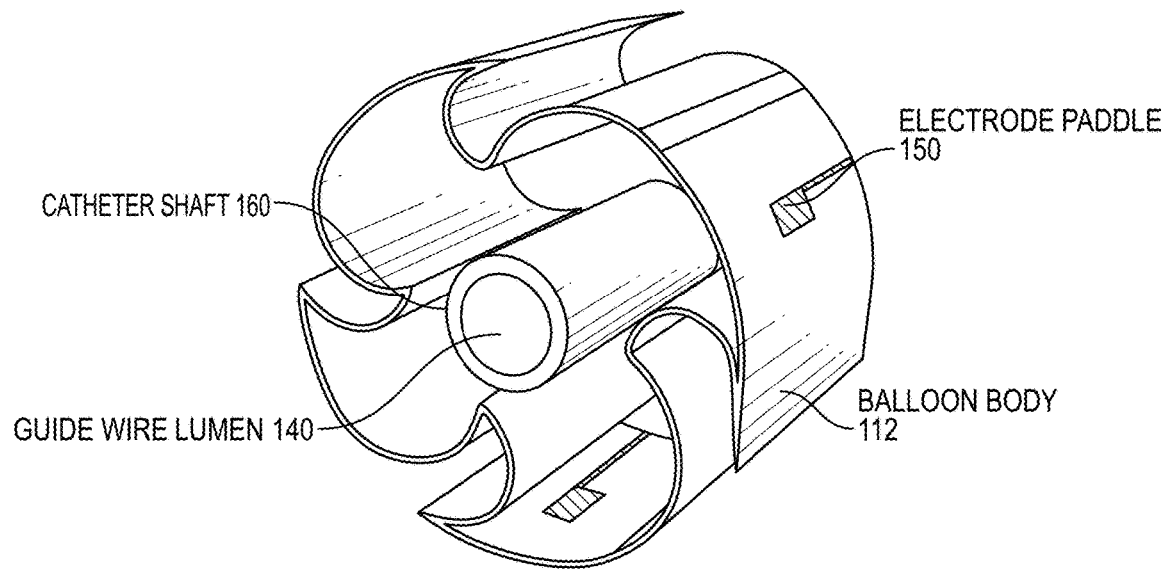
FIG. 1f: A cross section illustration of the angioplasty balloon at the cathode plate.
Figure 1G:
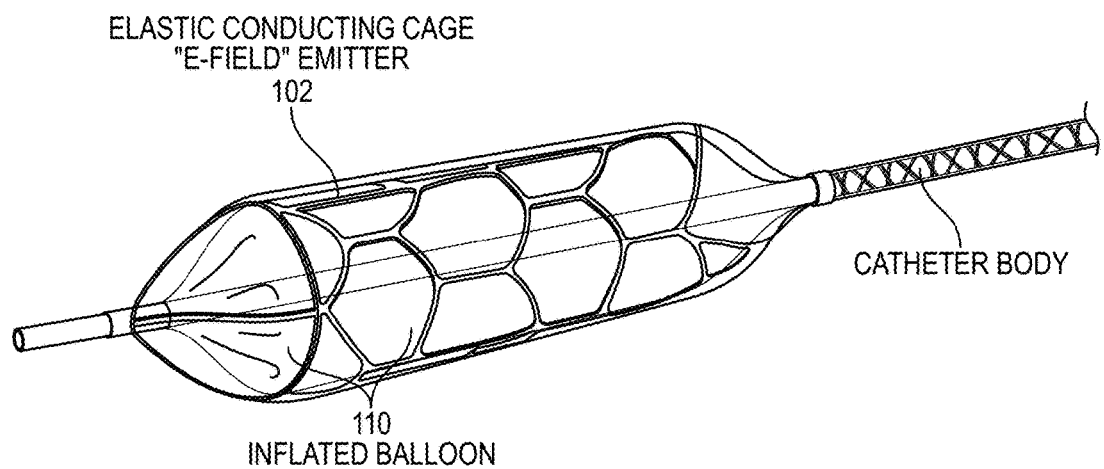
FIG. 1g. Representative illustration of the device and the composition of parts where an alternative configuration of elastic conducting cage is expanded with the balloon expansion. The balloon is encased by the cage and shown in this figure with connections to the conducting element comprising the catheter body. This drawing of the device illustrates the angioplasty balloon in the inflated form with the cage expanded the balloon. The catheter body is braided with an electrical conducting material from catheter hub to balloon body. Electrical conducting braids continue to the wire electrical connection on the hub end and extended to braid connections integrated into the cage.
Figure 2:
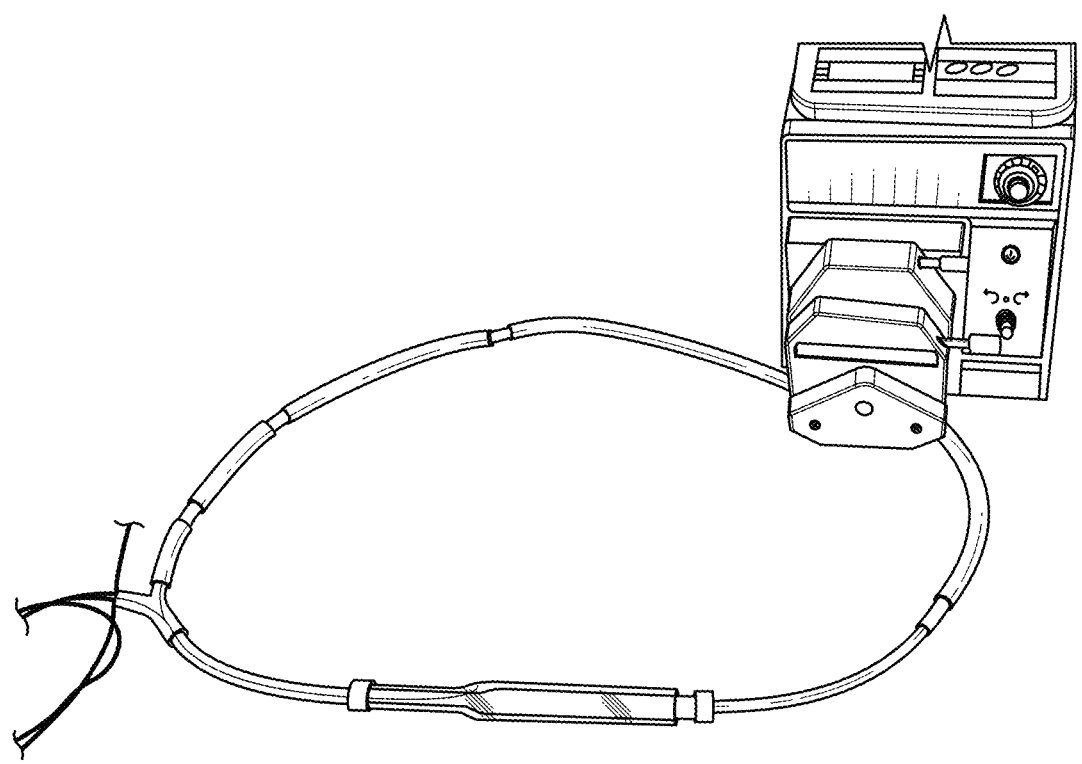
FIG. 2: This line drawing shows the setup of the closed loop circulation system as mentioned in this document to mimic the arterial blood flow exposed to test articles and artery. Closed loop fluid circulation system comprising isotonic media for tissue flow and experimentation. Tissue is inserted into the chamber and attached by canulas and allowed media flow through provided by the peristaltic pump. Device in implanted and deployed with or without electric field.
Figure 3:
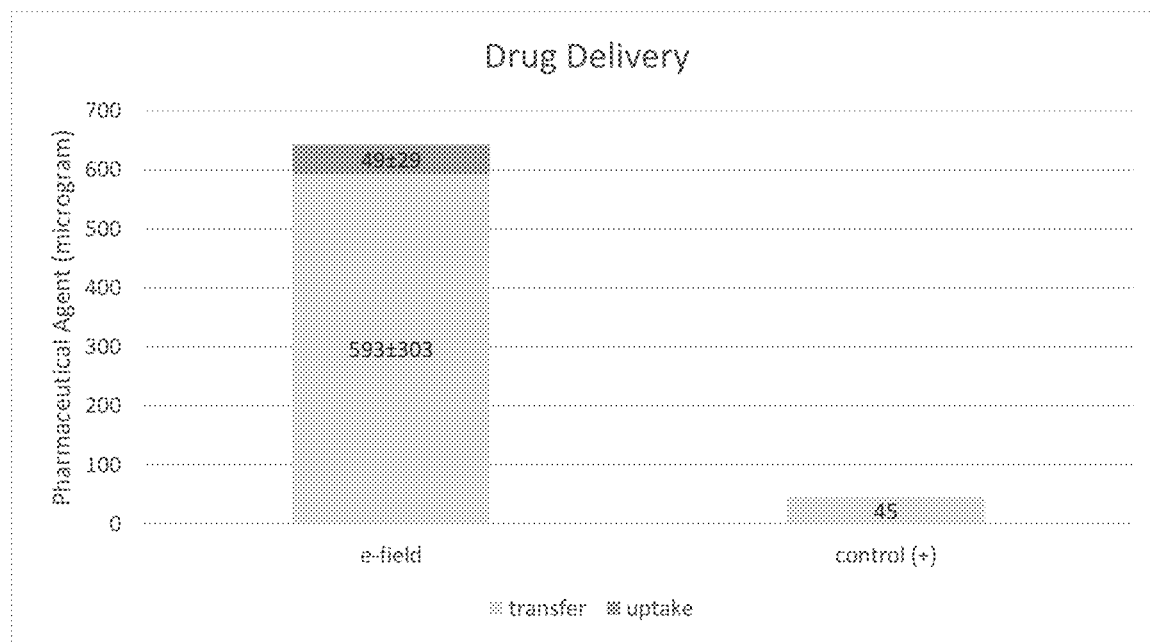
FIG. 3: Proof of concept data illustrating a comparison between the same device in use with and without electric field.
Figure 4:
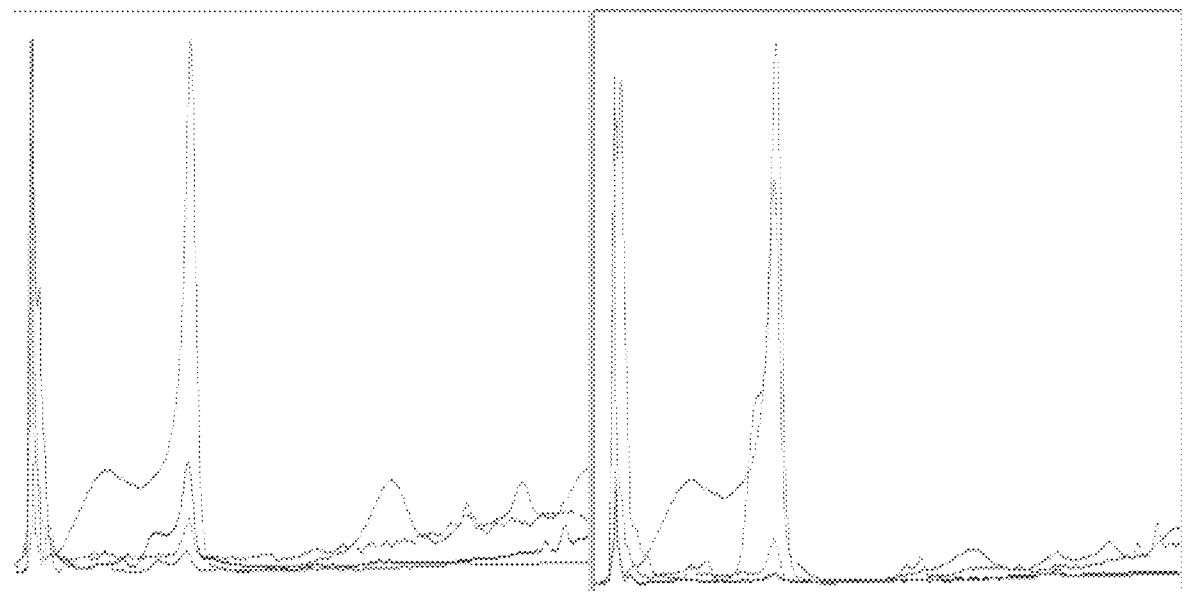
FIG. 4. A representative analysis is shown here where the results for the samples of interest are shown in the left panel as compared to the standard curve in the right panel.

Twelve Trireme Chocolate balloons (6.0×40) were coated as described above at surface paclitaxel concentration of 3.0 ug/mm2. Eight of the units were tested per the above protocol using the application of the GenePulser ll during balloon inflation in the arteries. Four of the units were deployed in identical arteries without the use of the GenePulserll, as a control. All of the arteries were tested for quantity of paclitaxel by HPLC. Results are listed graphically in FIG. 3 below. These data indicate that the application of voltage enhances the transfer of paclitaxel to arteries by a factor 10×.

What is claimed is:

1. A balloon catheter comprising:
   an elastic conducting alloy cage;
   a balloon that is encased within the elastic conducting alloy cage, wherein the elastic alloy cage is biased to be in a collapsed state on the balloon and is expandable by expansion of the balloon, and a working length of the balloon is coated with a coating including a therapeutic bio-active agent and an excipient; and
   a shaft having an electrode to provide a single polarity from an electrical power source to the elastic conducting alloy cage, wherein the elastic conducting alloy cage is to apply energy to a target tissue and emit an electric field to facilitate concurrent transfer of the bio-active agent from the coating on the working length of the balloon to the target tissue.

2. The balloon catheter of claim 1 wherein the elastic conducting alloy cage is formed from nitinol.

3. The balloon catheter of claim 1 wherein the electrical power source is to provide the single polarity to the elastic conducting alloy cage while an opposing polarity is grounded to the target tissue or a body part of an intended target.

4. The balloon catheter of claim 2 whereby the energy is primarily voltage driven with low current.

5. The balloon catheter of claim 1 whereby the electrical power source delivers a square wave with a voltage range of 0.001 kV to 5 kV.

6. The balloon catheter of claim 1, in which the bio-active agent is selected from the group of classes consisting of anti-neoplastic agents, mTOR inhibitors, taxanes, neurotoxins, steroids, and non-steroidal anti-inflammatory agents.

7. The balloon catheter of claim 4, wherein the excipient is selected from the group consisting of a polymer with hydrophilic character, an oligomer with hydrophilic character, a citrate ester, an adipate ester, a urea, a substituted urea, and a surfactant.

8. The balloon catheter of claim 1, wherein the elastic conducting alloy cage is coated with the coating.

9. The balloon catheter of claim 1, wherein the excipient is selected from the group consisting of a polymer with hydrophilic character and an oligomer with hydrophilic character.

10. The balloon catheter of claim 1, wherein the excipient comprises poly(ethyleneglycol).

11. The balloon catheter of claim 1, wherein the excipient is selected from the group consisting of a sorbitan mono oleate and a block co-polymer of PEO and PPO.

12. The balloon catheter of claim 1, wherein the excipient comprises an iodinated non-ionic contrast agent.

13. The balloon catheter of claim 1, wherein the excipient comprises shellac.

14. The balloon catheter of claim 1, wherein the excipient comprises a lipid.

15. The balloon catheter of claim 1, wherein the excipient comprises a phospholipid.

16. The balloon catheter of claim 1, wherein:
    the elastic conducting alloy cage is connected to both distal and proximal ends of the balloon and is electrically connected therebetween, and
    the elastic conducting alloy cage includes a continuous electrical path around a circumference of the working length of the balloon when the balloon is expanded.

17. The balloon catheter of claim 16, wherein the elastic conducting alloy cage is formed from nitinol.

18. The balloon catheter of claim 17, wherein the elastic conducting alloy cage is a stent-like cage comprising an arrangement of struts forming the continuous electrical path around the circumference of the working length of the balloon when the balloon is expanded.

19. A balloon catheter comprising:
    an expandable balloon;
    a coating on the expandable balloon, the coating including a therapeutic bio-active agent and an excipient;
    an elastic conducting alloy cage that is biased to be in a collapsed state on the expandable balloon and is expanded by expansion of the expandable balloon such that the expandable balloon is encased by the elastic conducting alloy cage; and
    a shaft having an electrode to provide a single polarity from an electrical power source to the elastic conducting alloy cage, wherein the elastic conducting alloy cage is to apply energy to a target tissue and emit an electric field to facilitate concurrent transfer of the bio-active agent from the coating on the expandable balloon to the target tissue when the expandable balloon and the elastic conducting alloy cage are expanded.

20. The balloon catheter of claim 19, wherein the elastic conducting alloy cage is a stent-like cage.

21. The balloon catheter of claim 20, wherein the expandable balloon and the elastic conducting alloy cage are coated with the coating.

22. The balloon catheter of claim 21, wherein the elastic conducting alloy cage is formed from nitinol.

23. The balloon catheter of claim 22, wherein the electrical power source is to provide the single polarity to the elastic conducting alloy cage while an opposing polarity is grounded to the target tissue or a body part of an intended target.

24. The balloon catheter of claim 19, wherein the elastic conducting alloy cage is connected to both distal and proximal ends of the balloon and is electrically connected therebetween.

25. The balloon catheter of claim 24, wherein the elastic conducting alloy cage includes a continuous electrical path around a circumference of the working length of the balloon when the balloon is expanded.

26. The balloon catheter of claim 25, wherein the elastic conducting alloy cage comprises an arrangement of electrically connected struts forming the continuous electrical path around the circumference of the working length of the balloon when the balloon is expanded.

* * * * *